US006949350B1

(12) United States Patent
Meyer-Almes

(10) Patent No.: US 6,949,350 B1
(45) Date of Patent: Sep. 27, 2005

(54) CHEMOSENSITIVITY DETERMINATION USING PHOSPHATIDYLSERINE

(75) Inventor: Franz-Josef Meyer-Almes, Iserlohn (DE)

(73) Assignee: Evotec Analytical Systems GmbH, Erkrath (DE)

( * ) Notice: Subject to any disclaimer, the term of this patent is extended or adjusted under 35 U.S.C. 154(b) by 0 days.

(21) Appl. No.: 09/856,185

(22) PCT Filed: Mar. 11, 2000

(86) PCT No.: PCT/EP00/02161

§ 371 (c)(1),
(2), (4) Date: Sep. 7, 2001

(87) PCT Pub. No.: WO00/54048

PCT Pub. Date: Sep. 14, 2000

(30) Foreign Application Priority Data

Mar. 12, 1999  (DE) ................................ 199 10 955
Apr. 30, 1999  (EP) ................................. 99108496

(51) Int. Cl.[7] .................... G01N 33/574; G01N 33/567
(52) U.S. Cl. ..................................... 435/7.23; 435/7.21
(58) Field of Search .............................. 435/7.23, 7.21

(56) References Cited

OTHER PUBLICATIONS

Scutte et al., "Annexin V binding assay as a tool to measure apoptosis in differentiated neuronal cells" J. Neuroscience Method 86 (1) : 63-69 (1998).*
Han Chong Toh et al., "Vinorelbine Induces Apoptosis and Caspase-3 (Cpp32) Expression in Leukemia and Lymphoma Cells: a Comparison with Vincristine", *Leukemia and Lymphoma, 31*, 195-208 (1998).
Vladimir D. Kravtsov et al., "Use of the Microculture Kinetic Assay of Apoptosis to Determine Chemosensitivities of Leukemmias", *Blood, 92*, 968-980 (1998).
Antonius W.M. Boersma et al., "Bax Upregulation is an Early Event in Cisplatin-Induced Apoptosis in Human Testicular Germ-cell Tumor Cell Line Nt2, as Quantitated by Flow Cytometry", *Cytometry, 27*, 275-282 (1997).

* cited by examiner

*Primary Examiner*—Sandra E. Saucier
(74) *Attorney, Agent, or Firm*—Jacobson Holman PLLC

(57) ABSTRACT

A method for determining the chemosensitivity of cells towards at least one substance by measuring the apoptosis induced by said at least one substance, wherein the cells are incubated essentially concurrently with at least one marker whose interaction with phosphatidylserine can be detected and with said at least one substance, and the interaction between the marker and phosphatidylserine is detected in a time-resolved manner.

21 Claims, 4 Drawing Sheets

CHEMOSENSITIVITY DETERMINATION USING PHOSPHATIDYLSERINE

Figure 1:
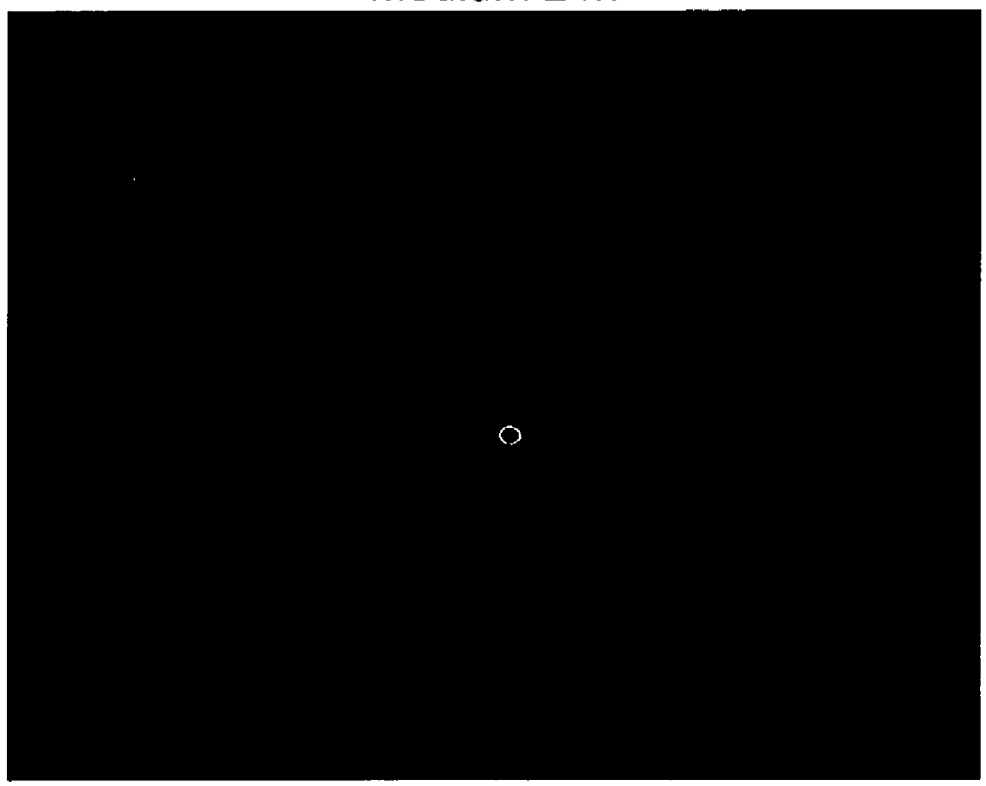

The present invention relates to a method for determining the chemosensitivity of cells towards at least one substance by measuring the apoptosis induced by said at least one substance.

Chemosensitivity Tests

Successful treatments and healings of tumor diseases have greatly increased in number since the introduction of chemotherapy. For example, the survival rate of infantile acute lymphatic leukemia (ALL) was less than 10% in the middle of the 1960s. Today, the chance of healing is above 70%. The medicaments, so-called cytostatic agents, are administered according to particular therapeutic plans alone or in combination with other active substances. By now, there are an immeasurable number of different therapeutic plans which have been established empirically and are constantly being developed further. The main criterion for an improved therapeutic plan is an improved survival rate (clinical outcome). This criterion is met by the majority of the patients. However, each individual has a different furnishing of cells with different properties. This is true, in particular, of the properties of tumor cells. In some studies, it could be shown that a therapy has an extremely good effect for one subpopulation while it is little effective or not effective at all for other patients because of drug-resistant tumors (Lacombe et al., Blood, 84, 716–723 (1994), Smit et al., International Journal of Cancer 51, 72–78 (1992)). It could be shown that not only the effectiveness of different medicaments but also the effective dose of one medicament can be different individually. Establishing the individual dosage of a medicament is important to patients in order to receive, on the one hand, as much medicaments as necessary for being healed and to keep, on the other hand, the toxic effects of the therapy and the probability of a secondary cancer disease induced by the chemotherapy as low as possible. Good as the currently usual therapeutic plans may be, progress in terms of average survival rate has been stagnating in recent years. A further significant improvement of chemotherapy should be possible by establishing individually matched therapeutic plans.

To approach these problems, some researchers have attempted to measure the individual sensitivity of patients' tumors towards cytostatic agents in vitro. Most chemosensitivity tests currently used are at least partially based on the agar tumor culture test developed by Salmon (Salmon et al., Science, 197, 461–463 (1977)). Such tests measure the proliferation of the cells.

A second type of chemosensitivity test comprises the exclusion of (fluorescent) dyes or the release of the radioactive chromium isotope $^{51}$Cr which measures the disruption of the cell membrane by the direct or indirect action of cytostatic agents. A modification of the earlier dye exclusion test is the so-called DiSC assay (Weisenthal, Kern, Oncology 5: 92–103 (1991)) which additionally differentiates between normal and tumor cells by a second dyeing process.

The third type of chemosensitivity tests determines parameters of cellular metabolism as a measure of damage done by cytostatic agents. This test type comprises the radiometric BACTEC test (von Hoff D., Forseth B., Warfel L., in Salmon Trent (Ed.), Human tumor cloning, pp. 656–657, Grune & Stratton, Orlando (1984)), the MTT test (Freund A. et al., European Journal of Cancer 34: 895–901 (1998), Kaspers G. J. L., Blood 92: 259–266 (1998), Pieters R. et al., Leukemia 12, 1344–1348 (1998), Klumper E. et al., British Journal of Haematology 93: 903–910 (1996), Hwang W. S. et al., Leukemia Research 17: 685–688 (1993)) and its variations, the ATP test (Kangas L., Gronroos M., Nieminen A., Medical Biology 62: 338–343 (1984)) and the so-called FCA test (Meitner P., Oncology 5: 75–81 (1991), Rotman B., Teplitz C., Dickinson K., Cozzolino J., Cellular and Developmental Biology 24: f1137–1146 (1988)).

Agar culture assays have a great disadvantage in that not all tumor cells by far will grow in the agar cultures. This is true, in particular, of lymphatic leukemias and lymphomas (Veerman A. J. P., Pieters R., British Journal of Haematology 74: 381–384 (1990)). In the best known representative of this assay type, the clonogenic assay, the percentage of cell populations which can be evaluated is as low as 30–40%. The cells have to grow for a very long time (10–20 days) before the evaluation is done. In addition, the expenditure of work is immense.

The dye exclusion tests and the $^{51}$Cr release test determine the proportion of cells having a defect cell membrane. These tests often include the fixation and subsequent microscopical evaluation of the cells or the measurement of the radioactivity in the supernatant. Since a rather rough parameter, the integrity of the cell membrane, is measured, such tests are non-specific and cannot distinguish between a specific anti-tumor activity of a substance and physical cell damage or cell damage caused by a substance, for example, by heavy erosion or oxidation. Consequently, test of this type give a positive result also with substances which generally cause damage to all cells and thus are not suitable as an anti-tumor medicament. The probably most telling test of the dye exclusion type is the DiSC test. In contrast to other dye exclusion tests, it is capable of differentiating between cell damage to tumor cells and to normal cells due to double staining. However, the double staining and subsequent microscopical evaluation are extremely time-consuming. In addition, the results vary as a function of the person performing the evaluation and the detail image evaluated with the microscope.

To radiometric tests, such as the $^{51}$Cr release test, the following applies quite generally: The use of radioactive isotopes in diagnostic tests is increasingly being avoided today because of the potential danger and the problems of disposal. In addition, by now, fluorescence and luminescence techniques can achieve the same sensitivities for a total duration of the test which is often even shorter.

Of the chemosensitivity tests making use of the metabolism of a cell as a measure of proliferation, the MTT test and its variations are used the most often. After 4 days of incubation of the cells with various cytostatic agents, the MTT test has a relatively short test duration of about 4 hours. In addition, 96 samples can be evaluated in parallel in a microtitration plate using an ELISA reading device. This ensures an acceptable throughput with a relatively low personnel expenditure. The MTT test is based on the conversion of 3-[4,5-dimethylthiazole-2-yl]-2,5-diphenyltetrazolium bromide into a blue formazan product. The conversion is catalyzed by dehydrogenases which are active only in living cells. The MTT test is dependent on a constitutive basic activity of the cells examined. However, it has been found that some cell types, e.g., particularly often some FAB subtypes of acute myeloic leukemia, have a highly reduced dehydrogenase activity (Santini V. et al., Hematological Oncology 7: 287–293 (1989)). Therefore, the chemosensitivity of these tumor cells cannot be evaluated with an MTT test. Another problem is the water-insoluble formazan crystals which form. They must be solubilized by the addition of organic solvents, such as dimethyl sulfoxide or isopropanol.

Former experience has shown that this causes problems with the reproducibility of the tests.

Apoptosis

From the works of various research groups (e.g., Sen S. et al., FEBS Lett. 307: 122–127, Darzynkiewicz et al., Cytometry 13: 795–808 (1992), Fulda S., Los M., Friesen C., Debatin K. M., Int. J. Cancer 76: 105–114 (1998)), it appears likely that cell death caused by cytostatic agents generally involves the mechanism of apoptosis. Apoptosis is a cell death programmed by the cell itself which can be induced by physiological factors in the organism or by chemicals, such as cytostatic agents. The programmed cell death plays an extraordinarily important role in the cytostasis, e.g., of the immune system. Thus, for example, T cells directed against endogenous structures are removed from the organism by apoptosis. Otherwise, symptoms of an autoimmune disease may appear, e.g., lupus erythematodes, arthritic diseases, or disease from a T-cell tumor. Substances like the tumor necrosis factor alpha, which is synthesized by macrophages, are natural indicators of apoptosis.

Apoptosis proceeds according to a programmed uniform scheme in which phosphatidylserine, which is normally present exclusively on the inner side of the cell membrane, is presented on the outer side (inversion) in a very early phase. This event occurs substantially earlier than the fragmentation of DNA and disruption of the cell membrane in the late stage of apoptosis, which occurs hours later.

In addition to cell death by apoptosis, there is another form of cell death, that is necrosis, which is induced, e.g., physically, by osmotic shock, erosion or oxidation. This is manifested by a heavy degenerative damage to the cell.

Medenica (U.S. Pat. No. 5,736,129) determines the extent of cellular damage from cytostatic agents by staining the cells with propidium iodide, followed by counting the stained cells in a FACS (fluorescence-activated cell sorter). However, this approach has the great disadvantage of not precisely differentiating between apoptosis and necrosis; consequently, it cannot make use of the specific mechanism of action of cytostatic agents. In addition, the number of cells required for a telling analysis is very high.

The recognition of phosphatidylserine presented on the cellular surface is highly suitable for the specific detection of apoptosis since the inversion of phosphatidylserine is a very early step of apoptosis, and the staining can be performed quickly and easily on both fixed and suspended cells. In previously described tests, annexin V is always used as a marker which binds phosphatidylserine. It is characterized by a very low Kd of $5 \times 10^{-10}$ M. The high dependency on calcium cations of the binding is a disadvantage. These tests all consist of an incubation phase with or without substances (e.g., cytostatic agents), sedimentation and washing in PBS, followed by resuspension in a calcium-containing staining buffer with labeled annexin V. The stained cells can subsequently be counted in a FACS or on a fluorescence microscope. Since all previous test protocols contain washing steps and are therefore classified as heterogeneous assays, these tests are relatively labor-intensive and prone to errors. These tests are all characterized in that apoptosis is measured at one particular time after induction by substances, which corresponds to an end-point measurement. Since apoptosis is a dynamic process which goes through a maximum which depends on both the substance examined and the cell type and then subsides into a secondary necrosis, it is not known a priori at which time the extent of apoptosis must be measured. It follows that, in principle, several samples with, for example, tumor cells subjected to different incubation times must be assayed for chemosensitivity for every patient.

This procedure can also be seen from a catalogue of Clontech from the year 1998/99, pages 71 to 74, in connection with the authentic execution protocol APO Alert® Annexin V.

In Leukemia and Lymphoma (1998), 31 (1–2), pages 195–208, H. C. TOH et al. describe a method for the detection of apoptosis through the binding of annexin V to lymphoma and T cell leukemia cells. The apoptosis is induced by vinorelbine and vincristine. This also involves an end-point measurement.

In Blood (1998), 92 (3), pages 968–980, V. D. Kravtsow et al. describe the determination of an apoptosis curve by a time-dependent measurement of the optical density of a sample. A marker is not used. This method covers a parameter which is indirectly associated with apoptosis and, in addition, is comparatively non-specific and prone to disturbance.

In Cytometry (1997), 27 (3), 275–282, A. W. M. Boersma et al. also describe an end-point measurement in which incubations containing apoptosis-inducers are interrupted at different times, and the extent of apoptosis in the respective samples is determined.

The phosphatidylserine tests described to date have not enabled an immediate measurement of the time course of apoptosis. With the previous test protocols, a series of experiments had to be performed for a particular combination of a cell type and a concentration of a substance in order to establish the time course of apoptosis. The expenditure of time and personnel as well as the cell material needed for such a test would be so high that the highly parallel testing of small amounts of cell material for chemosensitivity versus different concentrations of many substances has not been possible.

It has been the object of the present invention to overcome the mentioned drawbacks of the prior art.

This object is achieved by a method for determining the chemosensitivity of cells towards at least one substance by measuring the apoptosis induced by said at least one substance, wherein the cells are incubated essentially concurrently with at least one marker whose interaction with phosphatidylserine can be detected and with said at least one substance, and the interaction between the marker and phosphatidylserine is detected in a time-resolved manner.

The cells to be examined for chemosensitivity are incubated in the presence of the substances, i.e., concurrently or with marker molecules already applied. Thus, in contrast to the heterogeneous test protocols employed to date, this is a homogeneous test of the "mix and measure" type which enables the immediate measurement of the kinetics of the apoptotic process. When annexin V is employed as the marker, it must be ensured that the calcium ion concentration remains constant and within the optimum concentration throughout the measuring time. This can be achieved, for example, by buffering the calcium ion concentration. The dependence on calcium ions can be completely circumvented by using other annexins, annexin derivatives, annexin muteins, antibodies, Fab fragments, single-chain antibodies, aptamers and/or other proteins having binding sites for phosphatidylserine as a marker instead of annexin V.

Miniaturization is possible to further reduce the consumption of materials. It could be shown that cells can be kept in culture for some days in less than 10 µl of medium. The reduction of the number of cells per sample compartment to ≦1000 per test enables highly parallel analyses of samples with extremely few cells from patients, e.g., from fine needle biopsies. The low need of cells also permits the high throughput screening (HTS) of unknown substances for anti-tumor activity.

When the apoptosis of cells from pathological tissues is tested using phosphatidylserine inversion, it is advantageous to include in the test healthy cells from the tissue as well as the same cells with no added substance as references. In particular, it is appropriate to include in the test as a control a permanent cell line whose chemosensitivity is known, in order to document the functionality of the test and realize mistakes in the test performance.

The following substances, for example, may be used as said substances:

A) Cytostatic agents

Abrin, amethopterin, acivin, aclacinomycin A, alanine mustard, altretamine, aminoglutethimide, aminopterin, amsacrin (mAMSA), various anabolic steroids, anthrapyrazole, L-asparaginase, 5-axacytidine, Bacillus-calmette-guerin, bis-antrene, busereline, busulfane, butyryloxyethylglyoxaldithiosemicarbazone, camptothecine, carbamate ester, carzinophyllin, CCNU, chlorambucil, chloroethylmethylcyclohexylnitrosourea, chloroethylcyclohexylnitrosourea, chlorode-oxyadenosine, corticotropin, cyproterone acetate, chlorotrianisene, chlorozotozine, chromomycin A, cytosine arabinoside (Ara-C), BCNU, bleomycin, cis-platin, carboplatin, cladribine, cyclophosphamide, dactinomycin, daunomycin, daunorubicin, decarbacin, doxorubicin, DTIC, dehydroemitine, 4-demethoxydaunorubicin, demothydoxorubicin, deoxydoxorubicin, dexamethasone, dibromodulcitole, dichloromethotrexate, diethylstilbestrole, bis(2-chloropropyl)-DL-serine, doxifluridine, elliptinium acetate, 4'-epidoxorubicin, epirubicin, epoietin-alpha, erythropoietin, esorubicin, estradiole, etoposide, fluoxymesterone, flutamide, folic acid, fotemustine, ftorafur, 4-FU, fludarabine phosphate, 5-FU, floxuridine, galactitole, gallium nitrate, gosereline, G-CSF, GM-CSF, hydrea, hexamethylmelamine (HMM), hydrocortisone, hydroxyprogesterone, 4-hydroperoxycyclophosphamide, ICRf 159, idamycin, ifosfamide, immunoglobulin IGIV, interferon, cobalt proporphyrin complex, leucovorin calcium, leuprolide, levadopa, levothyroxine, lindane, liothyronine, liotrix, lomustine, levamisole, masoprocole, maytansine, menogaril, 6-mercaptopurine, methosalene, methylesterone, methyllomustine, mithracin, mithramycin, mitotane, mitoxanthrone, methotrexate (MTX), 6-MP, mechlorethamine hydrochloride, medroxyprogesterone, megestrole acetate, melphalane, mesna, mitomycin C, nandrolone, sodium phosphate P32, navelbine, neocarcinostatin, nitrofururazone, nHuIFNa, nHuIFNb, nHuIFNp, octreotide acetate, ondansetrone hydrochloride, disodium pamidronate, pentamethylmelamine (PMM), pentostatin, peptiochemio, plicamycin, prednimustine, probromane, procarbazine, profiromycin, paraplatin, prednisolone, prednisone, razoxane-rIFNa-2a, rubidazone, rIFNa-2b, rIFNb-1b, rIFNt-1b, rIL-2, rTNF, semustine, SPG 827 (podophylline derivative), spirogermanium, streptonigrine, somatostatin, streptozocin, tamoxifene, taxole, thio-TEPA, 6-thio-guanine, tenoposide, testolactone, testosterone, 3-TGDR, rTNF, thyroglobulin, thyrotropin, trilostane, uracil mustard, VP-16, vincristine (VCR), vinblastine (VBL), verapamil, vindesine, vinzelidine, vitamin A acid, vitamin A analogues, zinostatin.

B) Peptides and peptoids.
C) Nucleic acids and nucleic acid derivatives.
D) Peptide nucleic acids (PNAs).
E) Hybrides of RNAs, DNAs, PNAs and derivatives.

To recognize extracellular phosphatidylserine, cells must be incubated, in the presence of a marker, with the substances to be examined. These markers may be antibodies, $F_{ab}$ fragments, single-chain antibodies, aptamers and/or other proteins having binding sites for phosphatidylserine, such as annexins. These markers may comprise a dye portion, a colloidal precious metal, a radioactive isotope, and/or rare-earth metal chelates.

Detection is preferably effected by means of imaging methods, such as fluorescence detection methods, especially based on confocal or conventional microscopy. The intact fluorescence-labeled cells presenting phosphatidylserine are recorded, e.g., with a CCD camera, and subsequently counted using an image processing program. Cells which can be stained by a DNA dye, such as propidium iodide, are considered necrotic and subtracted from the number of cells fluorescence-labeled through phosphatidylserine, so that the number of the apoptotic cells is determined. This is then related to the total cell number which is established by automated image evaluation on a phase-contrast microscope. However, fluorescence correlation spectroscopy (FCS) and confocal fluorimetry would also be suitable, in which the concentration of the fluorescent marker molecules in the supernatant and/or on the cellular surface is measured, for example. When multiple staining is used, for example, by using a second marker or the same marker with a different fluorescent dye, cross-correlation or two-color coincidence fluorimetric measurements can be performed in the supernatant as well as on the cellular surface. In both methods, two different fluorescent dyes are simultaneously detected. In cross-correlation, the time-dependent fluorescence fluctuation signals of the two measuring channels are cross-correlated. In two-color coincidence fluorimetry, a positive signal is seen when and only when the two fluorescence signals occur simultaneously at the same place. Such two-color analyses can even enhance the specificity of the detection for phosphatidylserine inversion. Of particular benefit is the use of FIDA and PIDA as described in WO 98/16814 and PCT/EP 98/06165. Thus, the multiple binding of fluorescent marker molecules to apoptotic cells can be easily measured by the enhanced fluorescence emission. By the use of 2D-FIDA, the specificity can be further enhanced. A combination of the mentioned fluorescence measuring techniques with a relative movement between the sample and measuring volumes has shown a very high performance. Since very much more cells per unit time can be observed in this way, the signal statistics and thus the signal-to-noise ratio is drastically improved. In particular, a quantification of the binding of fluorescent marker molecules to cells is also possible then.

By the labeling of phosphatidylserine, apoptotic cells, but also cells having defect cell membranes, are stained because the phosphatidylserines on the inside of the cellular membranes also become accessible. When the time course of apoptosis is followed, at first, intact apoptotic cells are externally stained in an increased manner. Smaller apoptotic vesicles (apoptotic bodies), which are also stained, pinch off. In the end phase, apoptotic cells undergo transition to secondary necrosis and disintegrate. Necrotic cells are characterized in that their cell membranes disintegrate into fragments. Apoptosis must be distinguished from necrosis so that the activities of effective cytostatic agents, which all follow one apoptotic mechanism, are specifically detected. In order to distinguish between apoptotic and necrotic cells, markers for the exclusion of necrosis can be additionally employed together with the marker which binds phosphatidylserine, for example, dyes which interact with nucleic acids but cannot permeate intact cell membranes (e.g., propidium iodide, BOBO™ (Molecular Probes)).

The time course of apoptosis can thus be followed "online" using the labeling of phosphatidylserine.

Figure 2:
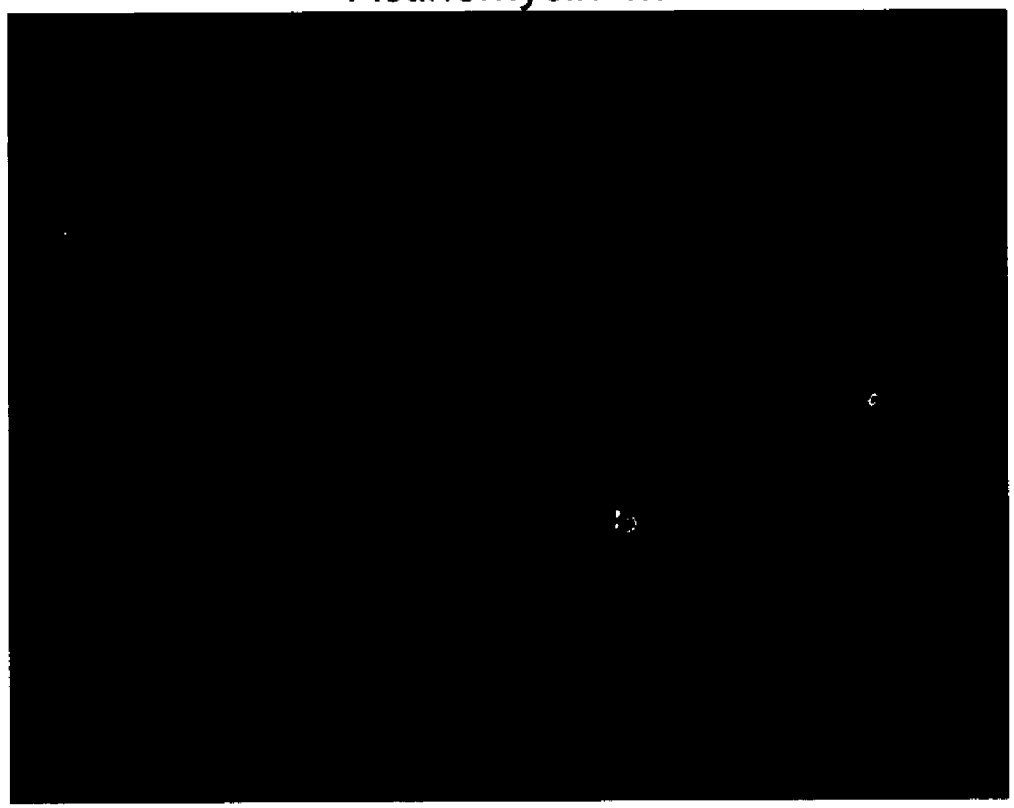
Figure 2:
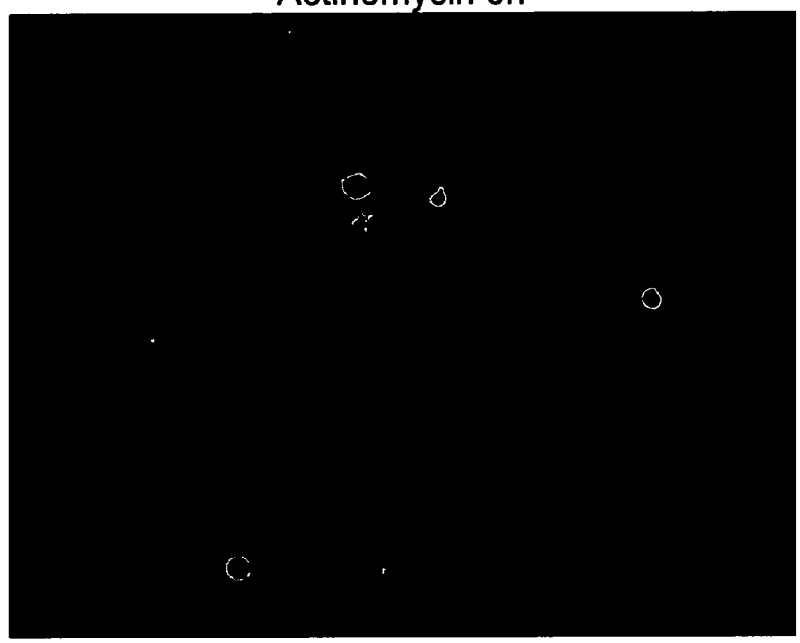
Figure 2:
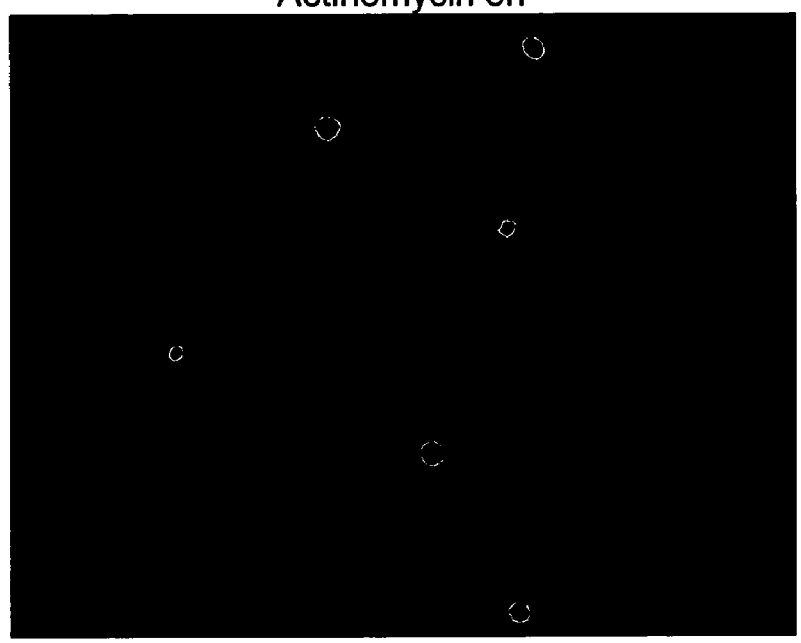
Figure 2:
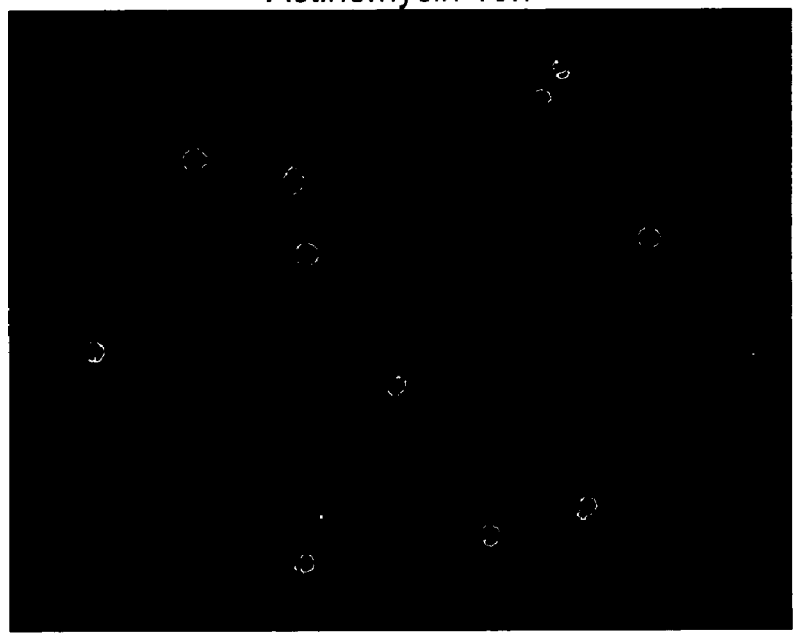
Figure 2:
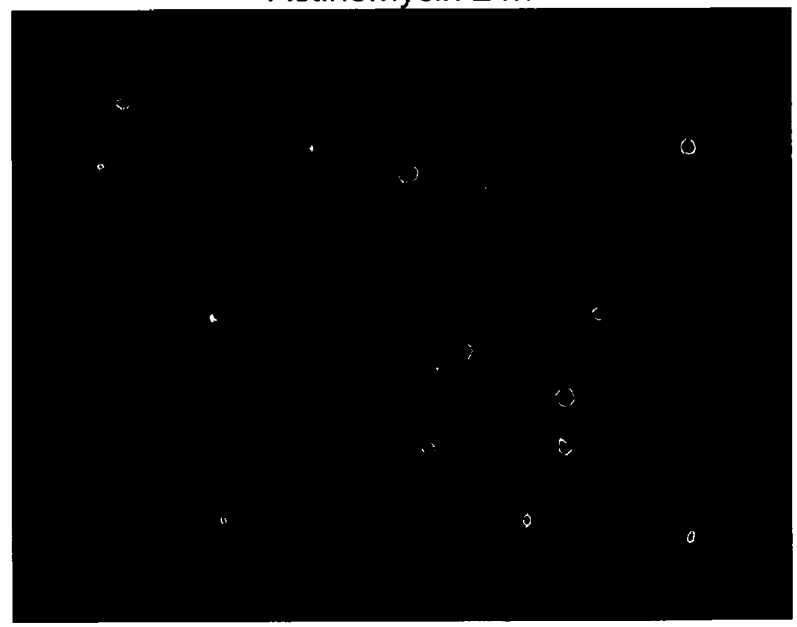

FIGS. 1 and 2 show fluorescence-micrographs of apoptotic cells (see Example 2).

It is important to standardize the extent of apoptosis for the total number of cells examined. This may be done, for example, by measuring the light absorption, scattered light, conductivity measurement, or microscopic evaluation. Standardization is necessary to be able to compare the extent of cellular damage caused by different cytostatic agents.

EXAMPLE

A highly potent cytostatic agent which immediately stops the growth of cells and induces all cells to undergo apoptosis can exhibit significantly less apoptosis, due to the low number of cells, than is exhibited by a less potent cytostatic agent in the presence of which the cells can still proliferate at first and undergo apoptosis only later and to a low extent. Only standardization considers apoptosis in relation to the total number of cells and evaluates the more potent cytostatic agent correctly.

The chemosensitivity testing of cells can be performed to particular advantage with the aid of a kit. This kit comprises a sample support with several sample compartments, each sample compartment containing at least one substance and a marker for phosphatidylserine detection and optionally a marker for the exclusion of necrosis. The sample support may be, for example, a commercially available microtitration plate. The substances to be tested and the marker may be present either as dry substances, in solution, or in the presence of matrix substances, such as salts, buffers, carbohydrates, carboxylic acids, pyrimidines, inorganic or organic nanoparticles with diameters of up to 1 $\mu$m.

Example 1

Materials for Performing the Chemosensitivity Test:
 sterile bench (Holten, Antares)
 fluorescence microscope (Carl Zeiss Jena)
 $CO_2$ incubator (WTC Binder)
 vortex mixer (Bender+Hobein AG)
 refrigerator (2–10° C.) (Bosch)
 freezer (−20° C.) (Liebherr)
 autoclave (H+P Labortechnik GmbH)
 centrifuge (Eppendorf)
 pipettes (Eppendorf)
 pipette tips (ratiolab)
 microtitration plates (96 wells) (Falcon)
 12.50 ml tubes (Falcon, Greiner)
 RPMI 1640 medium (Gibco)
 patient blood or bone marrow
 annexin V-Alexa 568™ (Boehringer Mannheim)
 BOBO™ (Molecular Probes)
 Dulbecco's PBS (Gibco)

Performance of the Test:

Determination of Cell Count

10 $\mu$l of a cell suspension is filled in a Neubauer chamber. Under a light microscope, the cells in the 16 smallest squares are counted. Multiplication of the cell count with 10,000 yields the number of cells per ml.

Preparation of Some Solutions of Cytostatic Agents

| Substance | Dissolving protocol |
|---|---|
| actinomycin D (Sigma A-1410) | 2 mg in 100 $\mu$l ethanol |
| cisplatin (Sigma P-4394) | 1 mg in 3.3 ml of fully desalted (FD) sterile water |
| doxorubicin (Sigma D-1515) | 1 mg in 1 ml of sterile FD water |
| methotrexate (Sigma M-9929) | 1 mg in 1 ml of DMSO + 1 ml of sterile FD water |
| cytosine arabinoside (Sigma C-1768) | 1 mg in 1 ml of sterile FD water |
| mitoxantrone (Sigma M-6546) | 2 mg in 1 ml of FD water |
| daunorubicin (Sigma D-8809) | 1 mg in 1 ml of PBS |
| prednisolone (Sigma P-6004) | 10 mg, dissolved in 1 ml of DMSO |

Mixing and Incubation with Cytostatic Agents

The cells are incubated with the cytostatic agents together with 0.5 $\mu$g/ml BOBO™ and 50 $\mu$M annexin V-Alexa 568™ in the presence of a constantly 3 mM calcium ion concentration.

Quantification on a Fluorescence Microscope

At one hour intervals, first the cells with red fluorescence labeling from annexin V, then the cells with green labeling from BOBO and finally the totality of the cells are counted for each sample in a phase-contrast mode on a fluorescence microscope equipped with a CCD camera and image evaluation software. The necrotic cells stained with BOBO are subtracted from the number of annexin V positive cells and related to the total number of cells to obtain the standardized percentage of apoptotic cells. In the course of the incubation time, the proportion of apoptotic cells increases first, but decreases again after some hours when more and more cells undergo transition into the final phase of apoptosis, i.e., secondary necrosis. The maximum extent of apoptosis is a measure of the effectiveness of a cytostatic agent.

Example 2

100,000 Jurkat P40 cells were simultaneously mixed with 1 $\mu$g/ml actinomycin D in the presence of 2 mM $CaCl_2$ and fluorescence-labeled annexin V and incubated at 37° C. in 5% $CO_2$ over a period of up to 24 h. After 4, 6, 8, 10 and 24 h, an aliquot was withdrawn, applied to a glass slide, fixed and analyzed by fluorescence microscopy. Even after 24 h, the medium control shows a very low spontaneous apoptosis rate with the staining of just 1 cell. In the course of the incubation time, the degree of apoptosis increases as seen from the increasing number of stained cells in the observation field. After 24 h, smaller cell fragments become visible which indicate secondary necrosis. When the time elapsed was extended and the cell destruction more advanced, there would be a time when fluorescent cell debris would no longer be visible. It was shown that apoptosis in a solution can be followed in a time-resolved manner by recording images at different times. The reaction mix was prepared at the beginning, and subsequently, the increasing apoptosis was only analyzed by means of imaging methods.

FIG. 1 shows the corresponding micrograph for the control with medium after 24 h. FIGS. 2a to 2e show the course after the addition of actinomycin.

What is claimed is:

1. A homogeneous method for determining the chemosensitivity of cells towards at least one substance in a sample by measuring the apoptosis induced by the at least one substance comprising the steps of:

incubating the cells essentially concurrently with at least one marker whose specific binding capability to phosphatidylserine can be detected and with the at least one substance, and detecting the binding between the marker and phosphatidylserine as a function of time in the sample.

2. A homogeneous method for determining the chemosensitivity of cells towards at least one substance in a sample by measuring the apoptosis induced by the at least one substance comprising the steps of:

adding to the cells at least one marker whose specific binding capability to phosphatidylserine can be detected, wherein the marker is added prior to or essentially concurrently with the at least one substance, incubating the cells with the at least one marker and with the at least one substance, and detecting the binding between the marker and phosphatidylserine as a function of time in the sample.

3. The method according to claim 2, wherein the cells are animal cells.

4. The method according to claim 3, wherein the cells are leukemia cells, cells of solid tumors, or cells of pathologic organs.

5. The method according to claim 2, wherein the cells are reference cells.

6. The method according to claim 5, wherein the reference cells are from non-pathological organs or from healthy regions of pathological organs.

7. The method according to claim 2 further comprising the steps of performing a reference measurement without the addition of the at least one substance.

8. The method according to claim 2 wherein the at least one substance is selected from the group consisting of pharmaceutically active substances, chemotherapeutic agents, environmental pollutants, peptides, nucleic acids and derivatives thereof, peptide nucleic acids, and nucleic acid hybrids.

9. The method according to claim 2 wherein the at least the marker is selected from the group consisting of antibodies, Fab fragments, single-chain antibodies, aptamers, and other proteins having binding sites for phosphatidylserine.

10. The method according to claim 2 wherein the said marker comprises a dye portion, a colloidal precious metal, a radioactive isotope, rare-earth metal chelate or a combination, thereof.

11. The method according to claim 2 wherein the detecting step distinguishes apoptotic cells from necrotic cells.

12. The method according to claim 11 further comprising the steps of co-incubating the cells with a marker for necrotic cells.

13. The method according to claim 12 wherein said marker for necrotic cells is a dye interacting with nucleic acids which cannot permeate intact cell membranes.

14. The method according to claim 2 wherein detecting is performed by an imaging method.

15. The method according to claim 14 wherein the imaging method comprises fluorescence detection.

16. The method according to claim 14 wherein the imaging method comprises confocal or conventional microscopy.

17. The method according to claim 2 further comprising the steps of standardizing the number of cells identified as apoptotic for the total number of cells.

18. The method according to claim 2 wherein the detecting step is performed with a time resolution of hours or at greater time intervals.

19. The method according to claim 2 wherein the marker is annexin V in the presence of calcium ion in a concentration range of from 0.1 to 30 mM.

20. The method according to claim 19 wherein the calcium ion concentration range is from 1 to 10 mM.

21. The method according to claim 2 used for screening for apoptotically effective substances.

* * * * *

UNITED STATES PATENT AND TRADEMARK OFFICE
CERTIFICATE OF CORRECTION

PATENT NO. : 6,949,350 B1
DATED : September 27, 2005
INVENTOR(S) : Meyer-Almes

It is certified that error appears in the above-identified patent and that said Letters Patent is hereby corrected as shown below:

Title page,
Item [73], Assignee, change "Evotec Analytical Systems GmbH" to -- Evotec Technologies GmbH --.

Signed and Sealed this

Fourteenth Day of March, 2006

JON W. DUDAS
*Director of the United States Patent and Trademark Office*